United States Patent [19]
Hall

[11] Patent Number: 5,219,324
[45] Date of Patent: Jun. 15, 1993

[54] ANTERIOR DORSAL ANKLE FOOT ORTHOSES

[76] Inventor: Charles Hall, 7035 N. 98th St., Milwaukee, Wis. 53224

[21] Appl. No.: 849,756

[22] Filed: Mar. 12, 1992

[51] Int. Cl.[5] .............................................. A61F 5/00
[52] U.S. Cl. ........................................ 602/28; 602/27
[58] Field of Search ....................... 602/27, 28, 29, 23, 602/5; 128/80 E, 80 H

[56] References Cited

U.S. PATENT DOCUMENTS

| | | | |
|---|---|---|---|
| 3,504,668 | 4/1970 | Boudon | 602/28 |
| 4,510,927 | 4/1985 | Peters | 602/27 |
| 4,665,904 | 5/1987 | Lerman | 602/27 |
| 4,862,900 | 9/1989 | Hefele | 602/27 |
| 4,982,733 | 1/1991 | Broadhurst et al. | 602/27 |

Primary Examiner—Richard J. Apley
Assistant Examiner—Beverly A. Meindl
Attorney, Agent, or Firm—Andrus, Sceales

[57] ABSTRACT

An orthopedic brace for foot drop and similar conditions utilizes an anterior dorsal ankle foot orthoses having an anterior support adapted to be placed against the shin of the leg and strapped to the leg at a point below the knee. The lower end of the orthoses terminates in a yoke at the dorsal portion of the foot, the yoke having lateral side members adapted to be placed on either side of the foot for supporting a foot pad. The foot pad supports the foot from the heel to the ball. The ankle/foot orthoses may be placed in standard footwear, reducing the visibility of the brace to the observer.

17 Claims, 1 Drawing Sheet

ANTERIOR DORSAL ANKLE FOOT ORTHOSES

BACKGROUND OF THE INVENTION

1. Field of the Invention

The invention is generally related to orthopedic braces and is specifically related to an ankle foot orthoses for drop foot and related ankle and foot conditions.

2. Description of the Prior Art

Drop foot and related conditions resulting from a paralysis or weakness of dorsi flexion muscles is often a condition experienced by stroke victims and can be brought on by other trauma, injuries and pathologies to the leg, foot and ankle, as well. Over the years, orthopedic braces have been developed to correct the condition, permitting a patient to walk and function in a relatively normal manner. Conventional braces used to correct drop foot conditions control and support the foot, but generally restrict motion about the ankle. The early braces were made of metal and included two solid bars which were placed on either side of the foot and extended upwardly along the inside and outside of the leg to a point below the knee. The upper end of the metal brace was then secured about the leg by use of a strap. The lower end of the metal brace was secured to a modified shoe and held the shoe in a generally horizontal position for supporting the foot.

The earliest braces of this type supported the shoe in a rigid position. This permitted the patient to walk and function in a generally normal manner with the foot rigidly held in place. Further developments incorporated a brace using the metal side members which fit inside the shoe and had a platform or base for supporting the foot. The base was often spring biased, permitting minimal flexing of the foot when walking, creating a more natural movement of the foot relative to the ankle and leg.

While these braces were functionally acceptable, the use of the metal side bars often created discomfort, were cosmetically unattractive, heavy and required the use of either modified or customized shoes in order to permit the brace to be attached to and properly support the foot.

With the advent of plastics, molded orthopedic braces became available. A molded orthopedic brace for foot drop was developed and was generally L-shaped in configuration, having a posterior support adapted to be placed against the back of the leg. The posterior support extended from a point below the knee to the heel of the patient, and included a contoured lower element which conformed to the bottom or plantar surface of the foot. The foot support base extended outwardly to the sides of the foot and forward from the heel toward the toes. The posterior brace was made of a unitary molded construction and generally held the foot in a rigid position. Because of the elevation of the foot by placing the brace behind the heel, and under the foot the patient was required to wear an enlarged or modified shoe in order to place the brace inside the shoe.

The plastic brace was also available in an articulating construction, wherein the foot base portion was a separate member hingedly connected to the posterior leg support. As with the earlier metal braces, the hinge was spring biased, to create a dynamic hinge permitting limited movement of the foot and ankle relative to the leg to simulate ankle movement during walking and other activities. An example of a hinged, articulated plastic orthotic brace is manufactured by Gaffney Technology of Hillsborough, Oreg.

The type of brace applied often depends on the severity of the condition and the patient's ability to function with an articulated brace or, where required, a rigid brace. Over the years, both the metal and plastic articulated and non-articulated braces have been incorporated as standard braces to be applied to correct for foot drop condition, with the specific brace being selected based on condition and on the patient's abilities.

While the posterior plastic braces provided some advantages over earlier metal braces and were cosmetically more desirable, the support of the foot from behind the heel is unnatural since the ankle muscular structure and tendons generally support the foot at the dorsal area. This was particularly true when the plastic posterior brace was allowed to articulate. The plastic posterior brace hinges the foot relative to the leg behind the heel rather than in front of the heel. Further, both the metal and plastic braces required the use of modified or in the least, enlarged shoes, generally making the condition and the brace obvious to even the most casual observer.

SUMMARY OF THE INVENTION

The subject invention is directed to an anterior dorsal ankle foot orthopedic brace for correcting a foot drop condition. Specifically, the brace of the subject invention includes an anterior support which is adapted to be placed in a position extending generally from the dorsal portion of the foot along the shin to a point below the knee. The base for supporting the foot is secured to the anterior support near the instep of the foot by using a yoke or stirrup which surrounds the dorsal portion of the foot and is attached to the anterior support. This permits the heel portion of the foot to be unobstructed, and allow the patient to wear standard shoes, eliminating the expense of modified foot wear and reducing the obviousness of the condition to the typical observer.

In addition, by attaching the foot brace to the leg support at the dorsal area of the foot, the foot movement and foot support more closely conform to the muscular and tendon structure of the ankle joint, resulting in a greater degree of comfort and efficiency to the patient.

Also, it has been found, by incorporating different plastic thicknesses and structures, limited flexing of the foot is achievable using an integral, one-piece structure, eliminating the need for bulky and expensive hinge structures.

In addition, by utilizing the stirrup or yoke surrounding the dorsal portion of the foot and supporting the foot on either side of the ankle, twisting and other side motions of the foot are better controlled without adding to the structure and without increasing the discomfort to the patient.

The anterior dorsal ankle foot orthoses of the subject invention permits the foot to be housed in a stirrup structure which is placed in front of the ankle and at the dorsal portion of the foot resulting in a much more natural fit and feel to the brace. By utilizing the more natural stirrup-type support, the thickness and weight of the support is generally reduced, resulting in less bulk, readily permitting most patients to wear standard footwear and greatly reducing the visibility of the brace. By supporting the foot in the dorsal area, the patient resumes a more normal gait when walking and performing other activities.

In its preferred form, the orthoses of the subject invention includes an anterior support having a lower end terminating just above the dorsal portion of the foot and an upper end terminating at a point below the knee. The anterior support is adapted to be placed in position on the leg along the shin and is strapped in place on the leg. A yoke or stirrup extends downwardly from the lower end of the anterior support on either side of the foot in front of the ankle for supporting a base adapted to receive the foot.

In the preferred embodiment, the base extends from heel to approximately the ball of the foot, leaving the toes free to flex and extend in a normal manner during walking and other activities. The brace may be customized to fit each particular patient. However, it has been found that standard form braces are widely adaptable to a variety of patient needs and conditions, reducing the cost of the brace to the individual where desired.

In the preferred embodiment of the invention, the strap includes a hook-and-loop type fastener pad permitting quick installation and removal of the brace with a minimum of instruction. The brace may be made of an integral, unitary construction using either thermoplastic material. Under normal circumstances it has been found that 3/16" generally permits the patient to wear standard footwear and greatly reducing the visibility of the brace when worn under clothing and shoes. Of course, thickness is a factor of need, patient size and application.

Where desired, the shape and thickness of the yoke or stirrup can be controlled to control the amount of flexion between the foot base and the leg support, depending on the severity of the condition of the patient.

It is, therefore, an object and feature of the subject invention to provide an orthopedic brace for correcting a foot drop condition.

It is another object and feature of the subject invention to provide an orthopedic brace which provides an anterior and dorsal support of the foot.

Another object and feature of the subject invention is to provide medial lateral, or side-to-side control against the ankle from rolling over.

It is an additional object and feature of the subject invention to provide for an orthopedic foot brace for correcting drop foot condition, while permitting the patient to wear normal footwear.

It is yet another object and feature of the subject invention to provide an anterior dorsal ankle foot orthoses supporting the foot in advance of the ankle and in the dorsal area for more closely conforming to the natural ankle foot skeletal and muscular structure.

It is an additional object and feature of the subject invention to provide for an anterior dorsal ankle foot orthoses of a unitary construction permitting flexure of the foot relative to the ankle without the use of hinged members and the like.

Other objects and features of the invention will be readily apparent from the accompanying drawings and detailed description of the preferred embodiment.

DETAILED DESCRIPTION OF THE PREFERRED EMBODIMENT

Figures 1, 2, 3, 4:
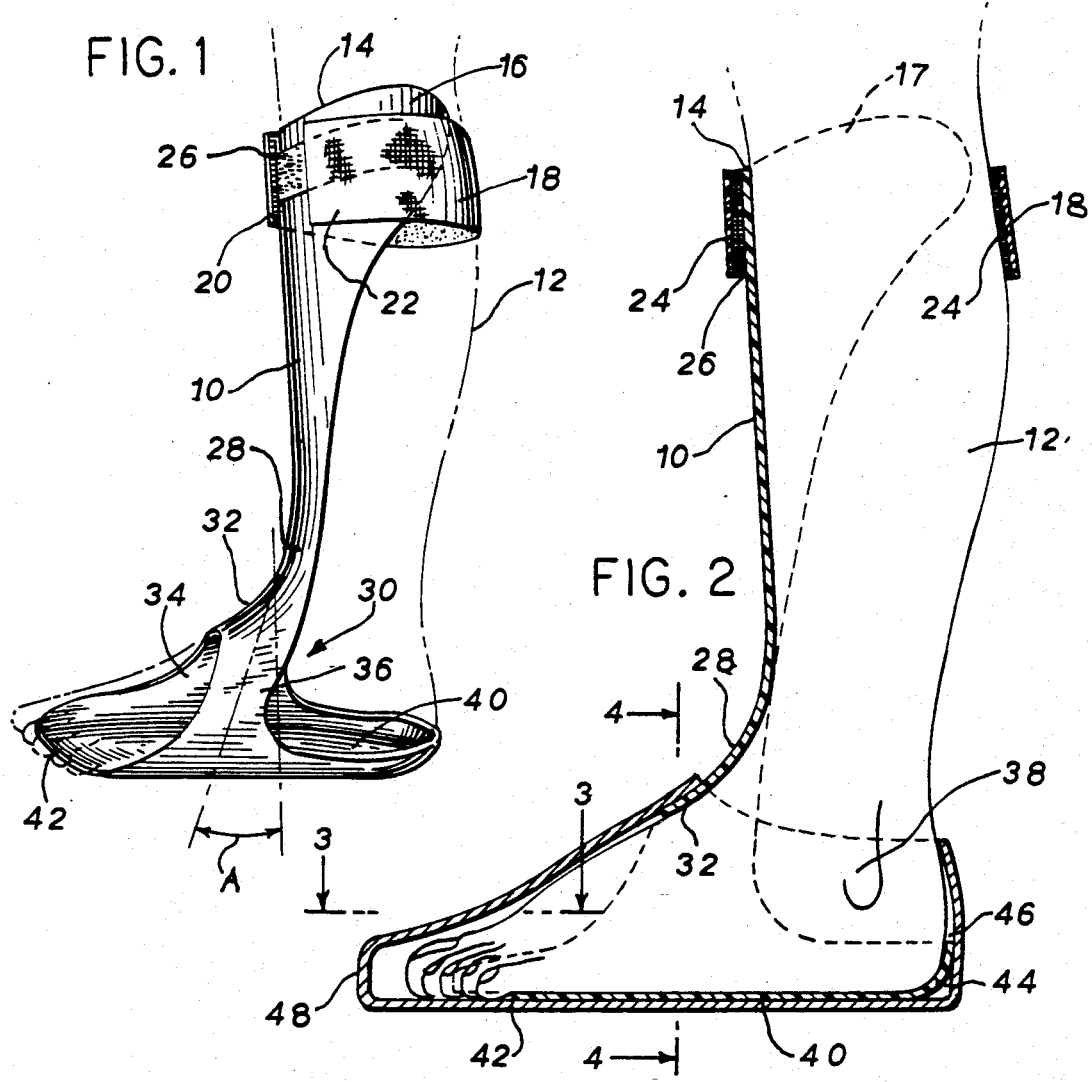
FIG. 1 is a perspective view of the anterior dorsal ankle foot orthoses of the subject invention.
FIG. 2 is a cross sectional view looking generally in the same direction as FIG. 1.
FIG. 3 is a fragmentary sectional view looking generally along the line 3—3 of FIG. 2.
FIG. 4 is a fragmentary sectional view looking generally along the line 4—4 of FIG. 2.

As shown in FIG. 1, the foot brace or foot orthoses of the subject invention includes an anterior support 10 which is contoured to fit along the leg 12 of the patient and to be positioned against the shin, as shown. The upper end 14 of the anterior support terminates at a point below the knee of the patient and is generally expanded as at 16 and 17 (FIG. 2) to provide good peripheral support and rigidity to the anterior support member for holding it securely against the leg. In the preferred embodiment, an elongated strap 18 has one end 20 which is secured to the front surface of the anterior support near the upper end 14 and another end 22 which is releasably secured to the support for wrapping the strap 18 around the leg 12 for securing the support thereon.

In the preferred embodiment, the strap 18 includes a hook-and-loop type fastener patch 24 or a material compatible with a similar fastener on the interior surface of the strap. The support 10 includes a compatible hook-and-loop type fastener patch 26. Both ends of the strap 20 and 22 may be readily secured to the patch 26 for securing the brace to the leg 12. Typically, the strap 18 is made of a flexible, non-stretchable material such as nylon or the like. Where desired, a limited stretchable material may be utilized to permit the strap to expand and contract with the leg during certain activities.

The lower end 28 of the anterior support terminates in a yoke or stirrup 30 which has a top pad 32 adapted to be placed over the dorsal portion of the foot and two elongated side members 34 and 36 which are adapted to extend downwardly from the dorsal pad 32 along either side of the foot in advance of the ankle joint 38 (FIG. 2). The lower end of each side member 34 and 36 supports the opposite sides of a foot pad or base 40.

In the preferred embodiment, the foot base 40 terminates at a front edge 42 just at the ball of the foot, permitting the toes to flex in a relatively normal manner while providing support for the foot. As shown in FIG. 3, the front end edge 42 may be contoured to conform to the natural shape of the foot. The rear end edge 44 of the foot base is upturned along a radius conforming substantially to the radius of the heel to provide a low rim 46. The rim 46 assures that the foot will not slip in the foot pad once the foot and leg are installed in the brace. Where desired, the rim 46 can continue along the side edges of the pad and into the side members 34 and 36 of the yoke 30 to provide a lateral support for the foot.

In the preferred form, the side members 34 and 36 are inclined forward from the dorsal end 28 of the anterior support toward the ball of the foot, shown by the included angle A (FIG. 1). This provides a natural feel for supporting the foot installed in the brace. As is particularly shown in FIG. 4, the yoke pad 32 and sides 34, 36 may be contoured to conform substantially to the natural contour of the dorsal and side portions of the foot, providing a comfortable fit.

It is an important feature of the invention that the orthoses of the subject invention may be readily received in standard footwear as indicated by the shoe 48 (FIG. 2). In a typical application, the patient would first put on socks, stockings or other normal clothing and then place the foot in the brace between the yoke and the footpad, with the heel against the heel ridge or rim 46 and a dorsal portion of the foot engaging the dorsal pad 32 of the yoke. The shoe 48 may then be placed on the foot in the normal manner. The strap 18 is placed around the leg with the opposite ends 20 and 22 secured to the fastener pad 26 for securing the orthoses to the leg. It has been found that a thin walled material such as thermoplastic having a thickness of 3/16" under normal circumstances is suitable for the brace and can be accommodated by most standard footwear. Of course, thickness is a factor of need, patient size and application.

The yoke of the preferred embodiment may be rigid or may be sufficiently flexible to permit the foot and leg to flex in a limited manner approximately at the lower dorsal end 28 of the anterior support 10. Depending on the condition of the patient, rigidity of the yoke can be controlled by the amount and thickness of the material of the brace in the area of the yoke pad 32 and the dorsal end 28 of the anterior support. Also, depending upon the condition of the patient, and the need for medial and lateral support, the rim 46 may be extended in height and the length of the foot pad (as controlled by the front end edge 42) may be altered to specific need.

The preferred embodiment of the orthoses of the subject invention is of a unitary molded construction made of a thermoplastic material, and where desired, may be heated for minor adjustment in form and shape. Custom orthoses may be made by utilizing a cast mold of the patient's foot and leg and constructing a custom molded brace therefrom. However, it has been found that a plurality of standardized braces are very effective for a large number of applications, greatly reducing the cost of the orthoses to the patient.

The anterior dorsal ankle foot orthoses of the subject invention provides an improved orthopedic brace for foot drop and similar conditions which has proven to be more comfortable than the posterior support braces of the prior art, providing the patient with a more normal feel. It is an added advantage of the particular configuration of the brace that it readily accepts normal footwear, greatly reducing the visibility of the brace and the patient's condition to the average observer.

While certain features and embodiments of the invention have been described in detail herein, the invention includes all modifications and enhancements within the scope and spirit of the following claims.

I claim:

1. An anterior dorsal ankle foot orthoses, comprising:
   a. an anterior support having a lower end and an upper end and being of sufficient length to be placed in a position extending generally from the dorsal portion of the foot along the shin to a point below the knee;
   b. a strap secured to the brace near the top of the anterior support and adapted for securing the anterior support to the leg;
   c. a yoke having a pair of continuous elongated sides, each including a top end secured to the lower end of the anterior support and a lower end, the yoke adapted to be placed around the dorsal and side portions of the foot; and
   d. including an integral footpad secured to the lower end of each side of the yoke for supporting the bottom of the foot when it is placed in the yoke, the footpad further including a rear end edge having an upstanding lip adapted to be positioned behind the heel of the foot.

2. The orthoses of claim 1, the footpad further including a front end positioned at the ball of the foot for permitting the toes to flex when the pad is in place.

3. The orthoses of claim 1, wherein said upstanding lip extends from the rear end edge and adapted for abutting against the back of the heel for preventing slippage of the pad relative to the foot.

4. The orthoses of claim 3, wherein said lip is defined by a radius conforming substantially to the curvature of the heel.

5. The orthoses of claim 4, wherein the foot pad includes side edges extending along the outer sides of the foot and wherein said upstanding rim extends forward from said rear end edge along said side edges of the foot pad and terminates at the elongated sides of said yoke.

6. The orthoses of claim 1, wherein the sides of the yoke are on a line intersecting the foot pad at an acute angle such that the upper end of the yoke is secured to the anterior support at the front of and adjacent the front portion of the ankle and the lower end of the yoke is secured to the foot pad at a position near the ball of the foot.

7. The orthoses of claim 1, wherein the anterior support includes a front outer surface and a back inner surface, and wherein the back inner surface is adapted to be placed against the shin of the leg.

8. The orthoses of claim 7, further including a strap secured to the front outer surface of the anterior support.

9. The orthoses of claim 8, the strap comprising an elongated flexible strip having opposite outer ends, one of said ends being permanently secured to the anterior support and the other of said ends adapted to the placed around the leg and releasably secured to the anterior support.

10. The orthoses of claim 9, further including a fastener secured to the front surface of the anterior orthoses and adapted for receiving and releasably securing said other end of the strap.

11. The orthoses of claim 10, wherein said fastener is a hook-and-loop type fastener pad and wherein said strap includes a compatible hook-and-loop pad adapted to mate with said fastener pad.

12. The orthoses of claim 11, wherein the strap is constructed of a flexible, non-stretchable material.

13. The orthoses of claim 1, wherein the unitary anterior support and base are constructed of thermoplastic material.

14. The orthoses of claim 1, wherein the unitary anterior support and orthoses are of a molded construction having a thickness of approximately 3/16".

15. The orthoses of claim 1, wherein the yoke is flexible, whereby the foot pad can move relative to the anterior support for simulating the natural flexing of the foot during a walking motion.

16. The orthoses of claim 1, wherein the anterior orthoses further includes a center section of a predetermined width limited generally to the width of the front of the shin and terminating in an upper end having side edges expanding outwardly from the predetermined width and contoured to wrap around a portion of the periphery of the leg.

17. The orthoses of claim 16, wherein the lower end of the anterior support is contoured to fit the dorsal portion of the foot.

* * * * *